(12) United States Patent
Bawendi et al.

(10) Patent No.: US 6,426,513 B1
(45) Date of Patent: Jul. 30, 2002

(54) WATER-SOLUBLE THIOL-CAPPED NANOCRYSTALS

(75) Inventors: Moungi G. Bawendi, Boston; Frederick V. Mikulec, Somerville, both of MA (US); Jin-Kyu Lee, Seoul (KR)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/156,457

(22) Filed: Sep. 18, 1998

(51) Int. Cl.$^7$ ............................................... H01L 31/00
(52) U.S. Cl. ............................................ 257/13; 257/17
(58) Field of Search ................................... 257/13, 17

(56) References Cited

U.S. PATENT DOCUMENTS

| | | | |
|---|---|---|---|
| 5,505,928 A | 4/1996 | Alivisatos et al. | 423/299 |
| 5,525,377 A | 6/1996 | Gallagher et al. | 427/512 |
| 5,751,018 A | 5/1998 | Alivisatos et al. | 257/64 |
| 5,906,670 A | * 5/1999 | Dobson | 257/17 |
| 5,990,479 A | * 11/1999 | Weiss | |

FOREIGN PATENT DOCUMENTS

| WO | 98/19963 | 5/1998 |
|---|---|---|

OTHER PUBLICATIONS

Lawless et al, *J. Phys. Chem* 1995 99 pp 10329–10335 "Bifunctional Capping in TiO$_2$".*

Chan, et. al., "Quantum Dot Bioconjugates for Ultrasensitive Nonisotopic Detection" *Science*, 281:2016–2018, 1998.

Spanhel, et al., "Photochemistry of Colloidal Semiconductors. Surface Modification and Stability of Strong Luminescing CdS Particles," *J. Am. Chem. Soc.* 109(19):5649–5655, 1987.

Kortan, et al., "Nucleation and Growth of CdSe on ZnS Quantum Crystallite Seeds, and Vice Versa, in Inverse Micelle Media," *J. Am. Chem. Soc.* 112:1327–1332, 1990.

Murray, et al., "Synthesis and Characterization of Nearly Monodisperse CdE (E=S, Se, Te) Semiconductor Nanocrystallites," *J. Am. Chem. Soc.* 115(19):8706–8715, 1993.

Rajh, et al., "Synthesis and Characterization of Surface–Modified Colloidal CdTe Quantum Dots," *J. Phys. Chem.* 97:11999–12003, Nov. 1993.

Lawless, et al., "Bifunctional Capping of CdS Nanoparticles and Bridging to TiO2," *J. Phys. Chem.* 99:10329–10335, 1995.

Dabbousi, et al., "Electroluminescence from CdSe quantum– dot/polymer composites," *Appl. Phys. Lett.* 66(11):1316–1318, Mar. 13 1995.

Alivisatos, "Perspectives on the Physical Chemistry of Semiconductor Nanocrystals," *J. Phys. Chem.* 1996(100):13226–13239, 1996.

Danek, et al., "Synthesis of Luminescent Thin–Film CdSe/ZnSe Quantum Dot Composites Using CdSe Quantum Dots Passivated with an Overlayer of ZnSe," *Chem. Mater.* 8(1):173–180, 1996.

(List continued on next page.)

*Primary Examiner*—Jerome Jackson, Jr.
(74) *Attorney, Agent, or Firm*—Choate, Hall & Stewart (57) ABSTRACT

A water soluble semiconductor nanocrystal capable of light emission is provided, including a quantum dot having a selected band gap energy, a layer overcoating the quantum dot, the overcoating layer comprised of a material having a band gap energy greater than that of the quantum dot, and an organic outer layer, the organic layer comprising a compound having the formula, $SH(CH_2)_nX$, where X is carboxylate or sulfonate. The particle size of the nanocrystal core is in the range of about 12 Å to about 150 Å, with a deviation of less than 10% in the core. The coated nanocrystal exhibits photoluminescence having quantum yields of greater than 10% in wate.

8 Claims, 4 Drawing Sheets

OTHER PUBLICATIONS

Liz–Marzan, et al., "Synthesis of Nanosized Gold–Silica Core–Shell Particles," *Langmuir* 12:4329–4335, 1996.

Matsumoto, et al., "Preparation of Monodisperse CdS Nanocrystals by Size Selective Photocorrosion," *J. Phys. Chem* 100(32):13781–13785, 1996.

Rogach, et al., "Synthesis and Characterization of Thiol–Stabilized CdTe Nanocrystals," *Ber. Bunsenges. Phys. Chem.* 100(11):1772–2778, 1996.

Hines, et al., "Synthesis and Characterization of Strongly Luminescing ZnS–Capped CdSe Nanocrystals, " *J. Phys. Chem.* 100:468–471, Jan. 1996.

Empedocles, et al., "Photoluminescence Spectroscopy of Single CdSe Nanocrystallite Quantum Dots," *Phys. Rev. Lett.* 77(18):3873–3876, Oct. 1996.

Nirmal, et al., "Fluorescence Intermittency in single Cadmium Selenide Nanocrystals," *Nature* 383:802–804, Oct. 1996.

Gan, et al., "Enhanced Photoluminscence and Characterization of Mn–Doped ZnS Nanocrystallites Synthesized in Microemulsion," *Langmuir* 1997(13):6427–6431, 1997.

Empedoles, et al., "Quantum–Confined Stark Effect in Single CdSe Nanocrystallite Quantum Dots," *Science* 278:2114–2117, Dec. 1997.

Kuno, et al., "The band edge luminescence of surface modified CdSe nanocrystallites: Probing the luminescing state," *J. Chem. Phys.* 106(23):9869–9882, Jun. 1997.

Dabbousi, et al., "(CdSe)ZnS core–shell quantum dots: synthesis and characterization of a size series of highly luminescent nanocrystallites," *J. of Phys. Chem. B* 101(46):9463–9475, Nov. 13 1997.

Fox, et al., "Fluorescence and Redox Activity of Probes Anchored through an Aminotrithiol to Polycrystalline Gold," *Langmuir* 14:816–820, 1998.

Mikulec, et al., "Fluorescent semiconductor nanocrystallites derivatized with biomolecules," *Amer. Chem. Soc. Nat'l Meeting*, Boston, MA, Aug. 24 1998.

Lett, "Color–Coding Quantum Dots Debut With Promising Careers In Clinical Diagnostics Field," :1–2, Sep. 25, 1998.

\* cited by examiner

WATER-SOLUBLE THIOL-CAPPED NANOCRYSTALS

This application is related to the following applications which were filed on even day herewith and which are incorporated in their entirety by reference: application entitled "Inventory Control" U.S. Ser. No. 09/160,458 and application entitled "Detection of Compounds and Interactions in Biological Systems Using Quantum Dots" U.S. Ser. No. 09/160,454.

The present invention was made with government support under Grant Number DMR-9400334 awarded by the National Science Foundation. The government has certain rights in the invention.

FIELD OF THE INVENTION

This invention relates to water-soluble nanocrystalline materials that emit visible light over narrow range of wavelengths.

BACKGROUND OF THE INVENTION

Semiconductor nanocrystals (quantum dots) whose radii are smaller than the bulk exciton Bohr radius constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of quantum dots shift to the blue (higher energies) as the size of the dots gets smaller.

Bawendi and co-workers have described a method of preparing monodisperse semiconductor nanocrystals by pyrolysis of organometallic reagents injected into a hot coordinating solvent (J. Am. Chem. Soc., 115:8706 (1993)). This permits temporally discrete nucleation and results in the controlled growth of macroscopic quantities of nanocrystals. Size selective precipitation of the crystallites from the growth solution can provide crystallites with even narrower size distributions. The narrow size distribution of the quantum dots allows the possibility of light emission in narrow spectral widths.

In an effort to improve the photoluminescent yield of the quantum dots, the nanocrystal surface has been passivated by reaction of the surface atoms of the quantum dots with organic passivating ligands, so as to eliminate energy levels at the surface of the crystallite which lie within the energetically forbidden gap of the bulk interior. These surface energy states act as traps for electrons and holes which degrade the luminescence properties of the material. Such passivation produces an atomically abrupt increase in the chemical potential at the interface of the semiconductor and passivating layer (See, A. P. Alivisatos, J. Phys. Chem. 100:13226 (1996)). Bawendi et al. (J. Am. Chem. Soc. 115:8706 (1993)) describe CdSe nanocrystals capped with organic moieties such as tri-n-octyl phosphine (TOP) and tri-n-octyl phosphine oxide (TOPO) with quantum yields as high as 20% in organic solvents such as toluene. See also, thesis of Christopher Murray, "Synthesis and Characterization of II–VI Quantum Dots and Their Assembly into 3-D Quantum Dot Superlattices", Massachusetts Institute of Technology, September, 1995; and Kuno et al. (J. Phys. Chem. 106(23):9869 (June, 1997)).

Although semiconductor nanocrystals prepared as described by Bawendi and co-workers exhibit near monodispersity, and hence, high color selectivity, the luminescence properties of the material is process dependent. The stability of the photoluminescent property of the nanocrystal is a function of the nature of the passivating species coating the outer surface of the nanocrystal. Known organically coated nanocrystals are not robust and exhibit degradation of photoluminescent yield in solution. This is likely due to dissociation of the passivating layer from the surface of the quantum dot or degradation of the passivating layer resulting in degradation of the semiconductor surface.

Passivation of quantum dots using inorganic materials also has been reported. Particles passivated with an inorganic coating are more robust than organically passivated dots and have greater tolerance to processing conditions necessary for their incorporation into devices. Previously reported inorganically passivated quantum dot structures include CdS-capped CdSe and CdSe-capped CdS (Than et al., J. Phys. Chem. 100:8927 (1996)); ZnS grown on CdS (Youn et al., J. Phys. Chem. 92:6320 (1988)); ZnS on CdSe and the inverse structure (Kortan et al., J. Am. Chem. Soc. 112:1327 (1990)); ZnS-capped CdSe nanocrystals (M. A. Hines and P. Guyot-Sionnest, J. Phys. Chem. 100:468 (1996); ZnSe-capped CdSe nanocrystals (Danek et al., Chem. Materials 8:173 (1996) and $SiO_2$ on Si (Wilson et al., Science 262:1242 (1993)).

Kortan et al. describes a ZnS capped-CdSe quantum dot which has a layer of thiolphenyl groups bound to the outer surface. The thiolphenyl groups were used to passivate the surface and to allow the clusters to be isolated in powder form. Lawless et al. reported the preparation of CdS semiconductor nanocrystals capped with bifunctional mercaptocarboxylic acids $HS(CH_2)_nCOOH$, where n=1–3. $TiO_2$ particles were attached to the CdS dots through the functional carboxylic acid group of the bifunctional capping moiety in order to promote interparticle electron transfer between dissimilar semiconductor particles.

The quantum dots described above are soluble or dispersible only in organic solvents, such as hexane or pyridine. Many applications which rely on the fluorescent emission of the quantum dots require that the quantum dots be water-soluble.

Many reported water-soluble quantum dots suffer from significant disadvantages which limit their wide applicability. For example, Spanhel et al. discloses a $Cd(OH)_2$-capped CdS sol (J. Am. Chem. Soc. 109:5649 (1987)); however, the photoluminescent properties of the sol were pH dependent. The sol could be prepared only in a very narrow pH range (pH 8–10) and exhibited a narrow fluorescence band only at a pH of greater than 10. Such pH dependency greatly limits the usefulness of the material; in particular, it is not appropriate for use in biological systems.

Other groups have replaced the organic passivating layer of the quantum dot with water-soluble moieties; however, the resultant derivatized quantum dots are not highly luminescent. Short chain thiols such as 2-mercaptoethanol and 1-thio-glycerol have been used as stabilizers in the preparation of water-soluble CdTe nanocrystals. See, Rogach et al., Ber. Bunsenges. Phys. Chem. 100:1772 (November, 1996) and Rajh et al., J. Phys. Chem. 97:11999 (November 1993). Other more exotic capping compounds have been reported with similar results. See, Coffer et al. Nanotechnology 3:69 (April, 1992) which describes the use of deoxyribonucleic acid (DNA) as a capping compound. In all of these systems, the coated quantum dots were not stable and photoluminescent properties degraded with time.

The unavailability of aqueous suspensions or solutions of quantum dots with sharp photoluminescent emissions limits their application in a variety of water-based applications, such as biological applications. In addition, aqueous solutions can often be very aggressive chemical systems and many of the known water-soluble quantum dots systems degrade, mainly by photoanodic decomposition at the semiconductor surface interface, during long exposure times in water. Thus there remains a need for water-soluble semiconductor nanocrystals which may be prepared as stable, robust suspensions or solutions in aqueous media. There is also a need for water-soluble quantum dots capable of energy emission with high quantum efficiencies, which possess a narrow particle size (and hence with narrow photoluminescence spectral range).

It is the object of the invention to provide water-soluble semiconductor nanocrystals (quantum dots) which overcome the limitations of the prior art and which exhibit high quantum yields with photoluminescence emissions of high spectral purity.

SUMMARY OF THE INVENTION

In one aspect of the invention, a water-soluble semiconductor nanocrystal capable of energy emission in the visible range is provided. The nanocrystal includes a quantum dot having a selected band gap energy overcoated with a layer of a material having a band gap energy greater than that of the quantum dot and with an appropriate band offset. An outer layer is found at the outer surface of the overcoating layer. The outer layer includes a compound having the formula, $SH(CH_2)_nX$, where X is carboxylate or sulfonate. The affinity of the sulfur group for the nanocrystal surface promotes coordination of the compound to the quantum dot outer surface and the carboxylic moiety, with an affinity for the aqueous medium, stabilizes the aqueous suspension. In preferred embodiments, the compound may have the formula, $HS(CH_2)_nCO_2H$ and salts thereof, where $n \geq 6$, preferably $n \geq 8$; and more preferably $n \geq 10$.

By "quantum dot" as that term is used herein, it is meant a semiconductor nanocrystal with size-dependent optical and electrical properties. In particular, the band gap energy of a quantum dot varies with the diameter of the crystal. In the naming convention used herein to refer to coated nanocrystals, the compound found within parentheses represents the core compound (i.e. the quantum dot), while the compound which follows represents the overcoated layer. "Quantum yield" as that term is used herein, means the ratio of photons emitted to that absorbed, e.g., the photoluminescence quantum yield.

In other embodiments of the invention, the coated nanocrystal is characterized in that the nanocrystal exhibits less than a 10% and preferably less than 5%, rms deviation in diameter of the core. The nanocrystal in an aqueous environment preferably exhibits photoluminescence having quantum yields of greater than 10%, and most preferably in the range of about 10 to 30%.

The invention permits the preparation of a water-soluble nanocrystal having a very narrow particle size distribution and exhibiting improvements in color purity and intensity of their photoluminescent emissions. Upon exposure to a primary light source, the quantum dot emits light of an energy characteristic of its composition and size.

These and other features and advantages of the invention are set forth in the description of the invention, which follows.

BRIEF DESCRIPTION OF THE DRAWING

The invention is described with reference to the figures, which are presented for the purpose of illustration only, and in which.

DETAILED DESCRIPTION OF THE INVENTION

Most prior art quantum dots are prepared in a coordinating solvent, resulting in the formation of a passivating organic layer on the dot surface comprised of the organic solvent. The passivated quantum dots thus are readily soluble in organic solvents, such as toluene, chloroform and hexane. The present invention provides a surface-modified particle that is soluble instead in aqueous media.

Figure 1:
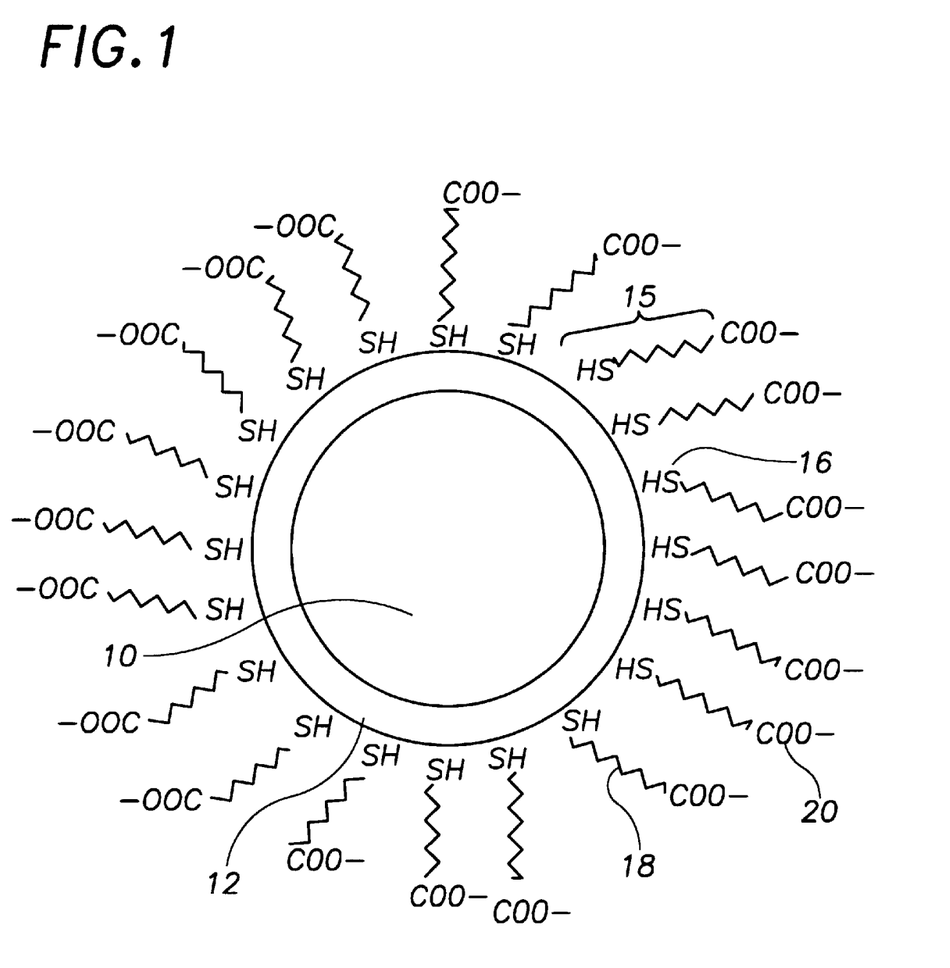
FIG. 1 is a schematic illustration of the water-soluble nanocrystal of the invention.

The nanocrystal is represented schematically in FIG. 1. A semiconductor nanocrystal 10 is coated with an outer layer 14 that renders the crystal water-soluble. The outer layer 14 further is selected to maintain the luminescent properties of the nanocrystal and to improve the robustness of the nanocrystal in aqueous solutions. An optional overcoating layer 12 may be used to coat the quantum dot before application of the outer layer 14. The outer layer includes a compound 15 of the formula, $SH(CH_2)_nX$, wherein X is carboxylate or sulfonate.

The nanocrystal includes a semiconductor nanocrystal that demonstrates quantum confinement effects in their luminescent properties. These nanocrystals are known as "quantum dots". When quantum dots are illuminated with a primary energy source, a secondary emission of energy occurs of a frequency that corresponds to the band gap of the semiconductor material used in the quantum dot. In quantum confined particles, the band gap is a function of the size of the nanocrystal.

Many semiconductors have been prepared as quantum sized particles and exhibit quantum confinement effects in their physical properties and can be used in the water-soluble nanocrystals of the invention. Exemplary materials suitable for use as quantum dots include ZnS, ZnSe, ZnTe, CdS, CdSe, CdTe, and ternary and quaternary mixtures thereof.

The semiconductor nanocrystals are characterized by their uniform nanometer size. By "nanometer" size, it is meant less than about 150 Angstroms (Å), and preferably in the range of 12–150 Å. The nanocrystal also is substantially monodisperse within the broad nanometer range given above. By monodisperse, as that term is used herein, it is meant a colloidal system in which the suspended particles have substantially identical size and shape. For the purposes of the present invention, monodisperse particles mean that at least 60% of the particles fall within a specified particle size range. In preferred embodiments, monodisperse particles deviate less than 10% in rms diameter, and preferably less than 5%. Monodisperse quantum dots have been described in detail in Murray et al. (*J. Am. Chem. Soc.,* 115:8706 (1993)), the thesis of Christopher Murray, Massachusetts Institute of Technology, September, 1995, supra, and Kuno et al., supra, which are hereby incorporated in their entireties by reference.

In preferred embodiments, the quantum dot has an overcoating layer. At the surface of the quantum dot, surface defects can result in traps for electron or holes that degrade the electrical and optical properties of the quantum dot. An insulating layer at the surface of the quantum dot provides an atomically abrupt jump in the chemical potential at the interface which eliminates energy states that can serve as traps for the electrons and holes. This results in higher efficiency in the luminescent process.

Suitable materials for the overcoating layer include semiconductors having a higher band gap energy than the quantum dot. In addition to having a band gap energy greater than the quantum dots, suitable materials for the overcoating layer should have good conduction and valence band offset with respect to the quantum dot. Thus, the conduction band is desirably higher and the valence band is desirably lower than those of the quantum dot. A material that has a band gap energy in the uv may be used. Exemplary materials include ZnS, GaN, and magnesium chalcogenides, e.g., MgS, MgSe and MgTe. The overcoating layer may include up to eight monolayers of the semiconductor material.

Particularly preferred quantum dots for emission in the visible include CdX, where X=S, Se and Te and ZnY, where Y=Se, Te. For those compounds, ZnS is a preferred material for use as the overcoating. For CdTe, ZnSe may be a preferred material for use as the overcoating due to the high degree of lattice match between the materials. A particularly preferred overcoated nanocrystal is described in Dabbousi et al. (*J. Phys. Chem. B* 101(46):9463 (1997)), and Kuno et al., supra, which are hereby incorporated in its entirety by reference.

According to the invention, the surface of the quantum dot is coated with the compound of the invention to stabilize the quantum dot in aqueous solution. The compound includes a sulfur group that attaches to the surface of the particle and a carboxylic acid group that is solvated in the aqueous media. The two groups are spanned by a hydrophobic region, $-(CH_2)_n-$. The hydrophobic region also provides a "pseudo-hydrophobic" environment for the nanocrystal and thereby shields it from its aqueous surroundings. To exhibit quantum size effects it is also necessary for the particles to remain electrically isolated from one another. The outer layer of the invention serves the additional useful purpose of maintaining the desired isolation between individual quantum dots.

The $-(CH_2)_n-$ group is selected to prevent photooxidation of the surface by charge transfer of a hole to the surface, whether from the core of the quantum dot or from the environment. Typical processes include electrolysis of water from the environment with the resultant oxidation of sulfur or selenium (of the quantum dot) to $SO_2$ or $SeO_2$, respectively. Transfer of a charge across the layer represents a non-energy emissive pathway for the excited state of the semiconductor and photoluminescence is thereby significantly reduced or quenched.

Prior art surface modifications of quantum dots included capping of CdS nanocrystals with 2-mercaptoethanol, 1-thioglycerol and 3-mercaptopropionic acid. See, Lawless, et al. and Rogach et al. These short chain organic molecules do not provide a luminescent, water-soluble quantum dot because the short carbon chain does not provide adequate insulation of the quantum dot to photooxidative processes. Therefore, charge transfer occurs between the quantum dot and either the carboxylate or the aqueous environment. Luminescence is thereby quenched. Consequently, quantum yields are "unacceptably low", i.e., less than 1%, in systems employing short chain organic molecules as a capping layer.

According to the invention, the hydrophobic region is preferably a long chain hydrocarbon moiety, $-(CH_2)_n-$, where n is greater than six and preferably greater than eight. Hydrocarbon moieties of n=11 and 15 have been successfully used in the manufacture of the water-soluble nanocrystal of the invention. There is no upper limit to the hydrocarbon chain length; however, it is recognized that very long hydrocarbon chains might render the nanocrystal undesirably "greasy". The hydrophobic region also may include branching hydrocarbons.

A method for the preparation of the water-soluble nanocrystal follows. The method is described for a (CdSe)ZnS quantum dot, but it is understood that the method may be applied in the preparation of quantum dots from the known semiconductor materials.

A population of nearly monodisperse nanocrystals first is prepared. The actual size of the nanocrystals will vary dependant upon the material used. For CdSe, particles range in size from about 12 Å to about 150 Å with a particle size distribution of about 5–10%. The monodisperse nanocrystals may be obtained by using a high temperature colloidal growth process, followed by size selective precipitation. In those instances where narrow spectral emission bandwidths are desired, it is desirable to use size selective precipitation to obtain a population of quantum dots of narrow particle size distribution. The interested reader is directed to Murray et al., supra, and the thesis of Christopher Murray, for further information.

The quantum dot may then be coated with the appropriate semiconductor overcoating layer. The coated nanocrystal may be prepared by introducing the substantially monodisperse first semiconductor nanocrystal and a precursor capable of thermal conversion into a second semiconductor material into a coordinating solvent. The coordinating solvent is maintained at a temperature sufficient to convert the precursor into the second semiconductor material yet insufficient to substantially alter the monodispersity of the first semiconducting nanocrystal and the second semiconducting material has a band gap greater than the first semiconducting nanocrystal. An overcoating of the second semiconductor material is formed on the first semiconducting nanocrystal. The monodispersity of the nanocrystal is monitored during conversion of the precursor and overcoating of the first semiconductor nanocrystal. The particle size distribution may be further refined by size selective precipitation. Further details in the preparation of a coated quantum dot for use in the water-soluble nanocrystal of the invention may be found in U.S. Ser. No. 08/969,302, filed Nov. 13, 1997 and entitled "Highly Luminescent Color-Selective Materials", and Dabbousi et al., supra, which are incorporated in their entirety by reference.

The outer surface of the nanocrystal, as formed, includes an organic layer derived from the coordinating solvent used during the capping layer growth process. The nanocrystal surface may be modified to obtain the water-soluble nanocrystal of the invention by repeated exposure to an excess of a competing coordinating group. For example, a dispersion of the quantum dot may be treated with a coordinating organic compound, such as those described herein, to produce nanocrystals which dispersed readily in water, but which no longer disperse in aliphatics. Such a surface exchange process may be carried out using a variety of compounds which are capable of coordinating or bonding to the outer surface of the capped quantum dot, such as by way of example, phosphines, thiols, amines, phosphine oxides and amine oxides.

Figure 2:
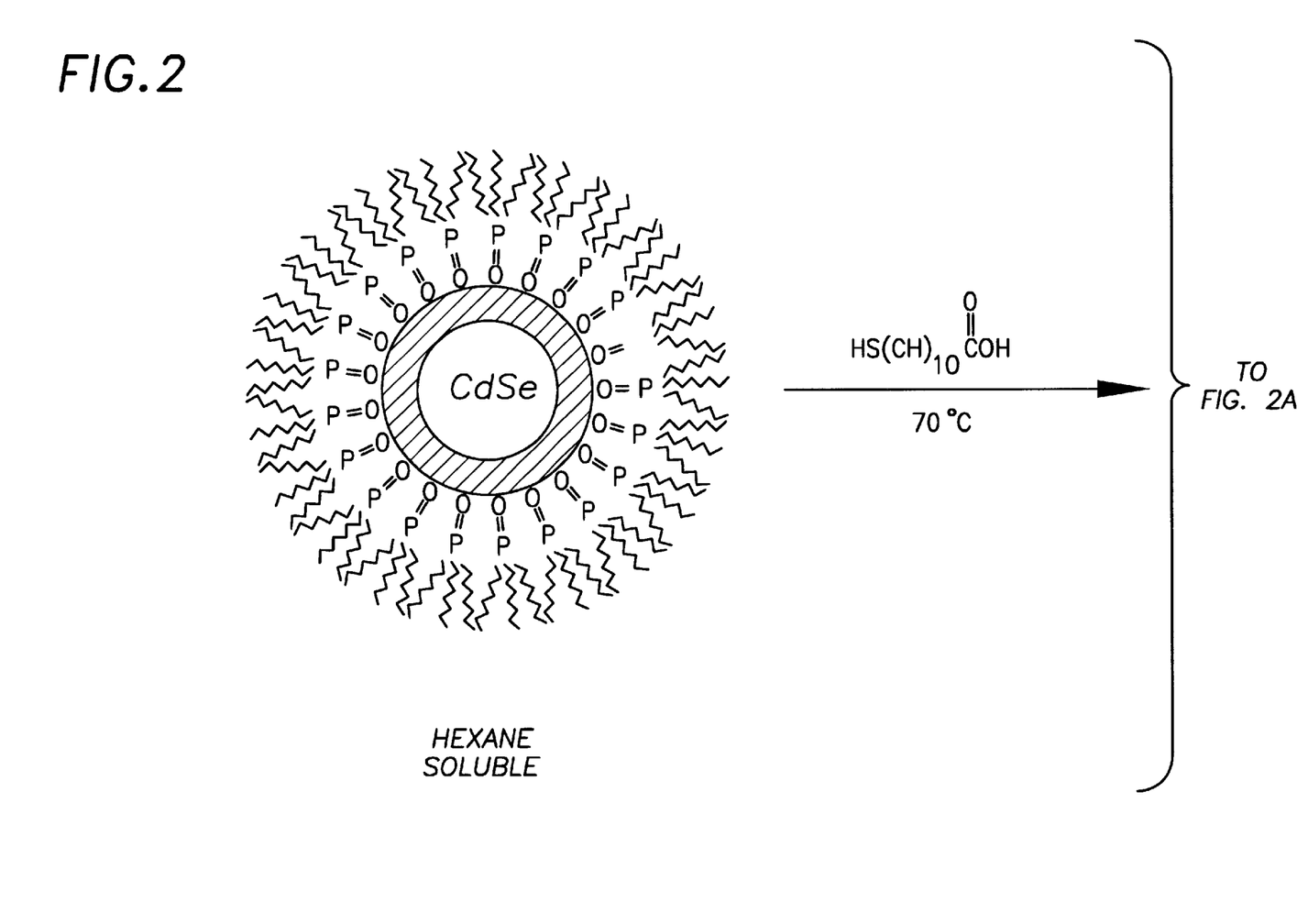
FIG. 2 is an illustration of the displacement reaction used in the formation of the water-soluble nanocrystal of the invention
Figure 2A:
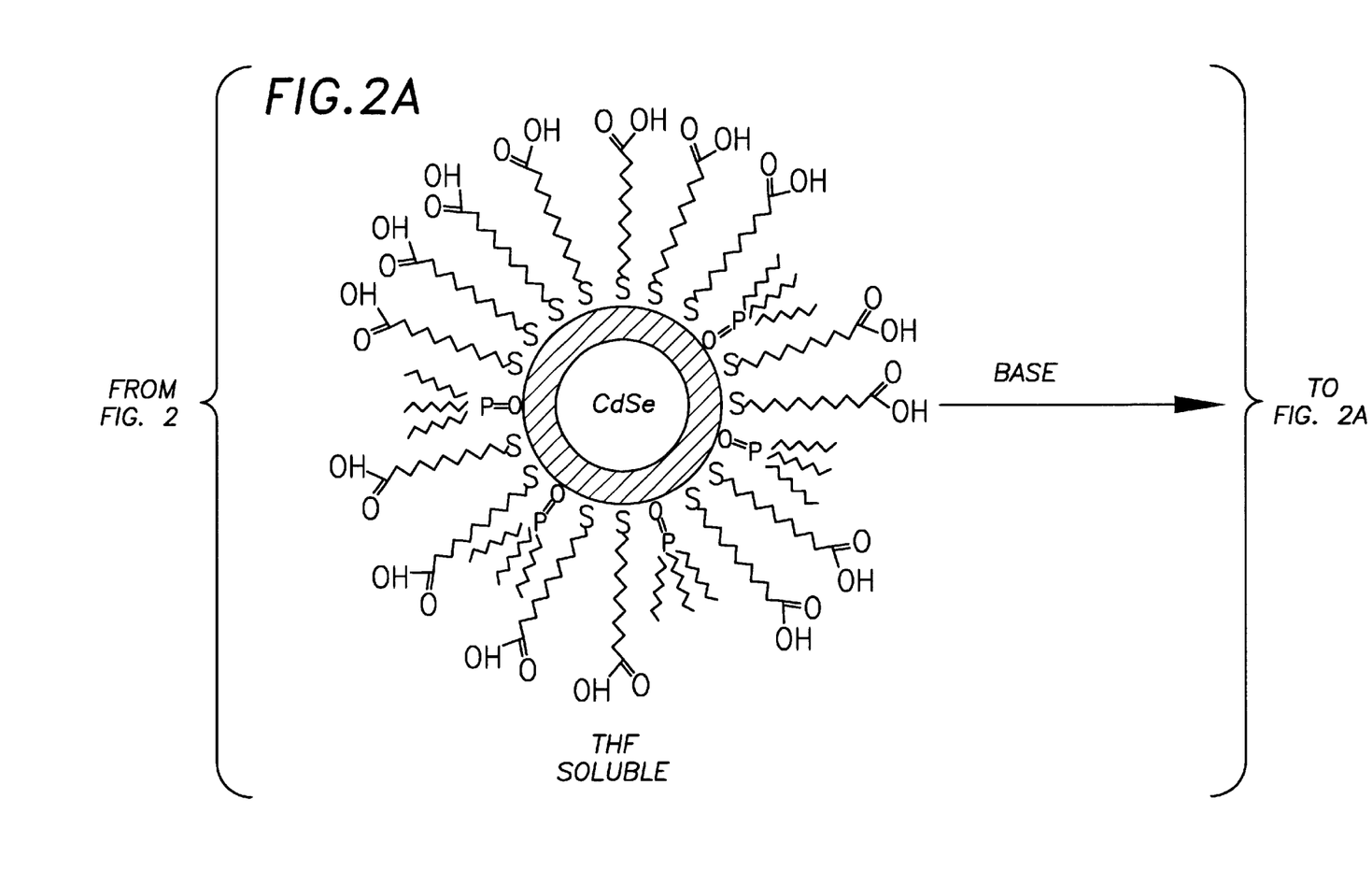
Figure 2B:
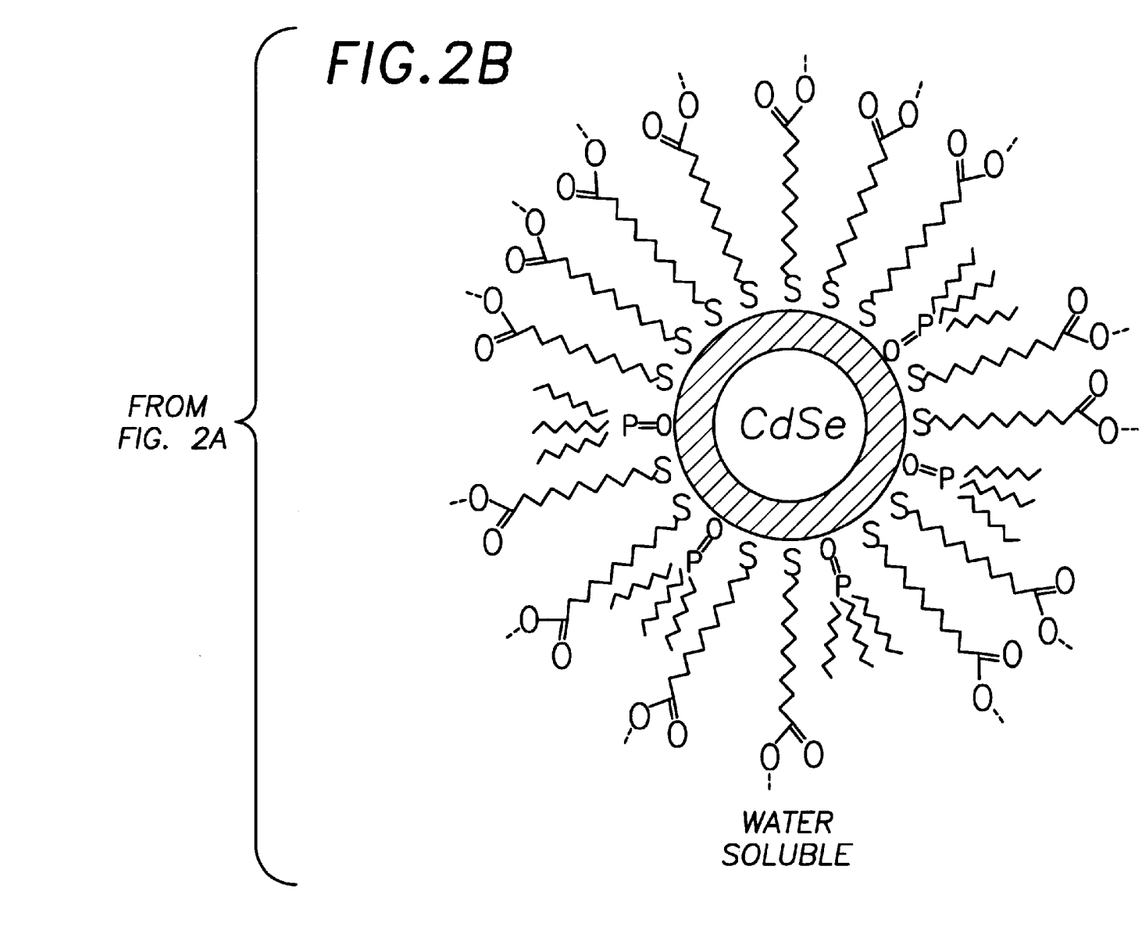

A typical reaction is shown in FIG. 2. Quantum dots 60 are prepared in a coordinating organic solvent such as trioctylphosphine oxide (TOPO) which results in the formation of a passivating TOPO layer 62 on the semiconductor surface of the quantum dot. This layer is displaced at least in part by the compound 54, a long chain mercaptocarboxylic acid, comprising the outer layer of the invention in order to obtain water-soluble nanocrystal 66. Displacement may occur by dispersion of quantum dots or overcoated quantum dots in medium containing high concentrations of the ligand used to form the outer coating. The medium may be a neat liquid comprising the ligand or it may be a highly concentration solution. High concentrations drive the displacement reaction forward to maximize surface coverage of the nanocrystal by the compound of the outer coating. Note that the displacement of the TOPO layer need not be complete in order to obtain a water-soluble nanocrystal.

It may be desirable to repeatedly expose the nanocrystal to the coordinating ligand solution. The outer coating may be comprised of a mixture of the original polar organic solvent used in the preparation of the nanocrystal and the water-solubilizing compound used in the outer coating of the invention. Substitution of the water-solubilizing compound need only be sufficient to render the compound water-soluble and need not be complete. In some embodiments, substitution is about 25–50% complete, preferably greater than 60% complete.

The example is illustrated in the following examples, which are presented for the purpose of illustration only and which are not limiting of the invention.

EXAMPLE 1

Preparation of TOPO Capped-(CdSe, ZnS (a) Preparation of CdSe

Trioctylphosphine oxide (TOPO, 90% pure) and trioctylphosphine (TOP, 95% pure) were obtained from Strem and Fluka, respectively. Dimethyl cadmium ($CdMe_2$) and diethyl zinc ($ZnEt_2$) were purchased from Alfa and Fluka, respectively, and both materials were filtered separately through a 0.2:m filter in an inert atmosphere box. Trioctylphosphine selenide was prepare by dissolving 0.1 mols of Se shot in 100 ml of TOP thus producing a 1M solution of TOPSe. Hexamethyl(disilathiane) ($TMS_2S$) was used as purchased from Aldrich. HPLC grade n-hexane, methanol, pyridine and n-butanol were purchased from EM Sciences.

The typical preparation of TOP/TOPO capped CdSe nanocrystals follows. TOPO (30 g) was placed in a flask and dried under vacuum (~1 Torr) at 180° C. for 1 hour. The flask was then filled with nitrogen and heated to 350° C. In an inert atmosphere drybox the following injection solution was prepared: $CdMe_2$ (200 microliters, 2.78 mmol), 1 M TOPSe solution (4.0 mL, 4.0 mmol), and TOP (16 mL). The injection solution was thoroughly mixed, loaded into a syringe, and removed from the drybox.

The heat was removed from the reaction flask and the reagent mixture was delivered into the vigorously stirring TOPO with a single continuous injection. This produces a deep yellow/orange solution with a sharp absorption feature at 470–500 nm and a sudden temperature decrease to ~240° C. Heating was restored to the reaction flask and the temperature was gradually raised to 260–280° C.

Aliquots of the reaction solution were removed at regular intervals (5–10 min) and absorption spectra taken to monitor the growth of the crystallites. The best samples were prepared over a period of a few hours steady growth by modulating the growth temperature in response to changes in the size distribution, as estimated from the sharpness of the features in the absorption spectra. The temperature was lowered 5–10° C. in response to an increase in the size distribution. Alternatively, the reaction can also be stopped at this point. When growth appears to stop, the temperature is raised 5–10° C. When the desired absorption characteristics were observed, the reaction flask was allowed to cool to ~60° C. and °mL of butanol were added to prevent solidification of the TOPO. Addition of a large excess of methanol causes the particles to flocculate. The flocculate was separated from the supernatant liquid by centrifugation; the resulting powder can be dispersed in a variety of organic solvents (alkanes, ethers, chloroform, tetrahydrofuran, toluene, etc.) to produce an optically clear solution.

(b) Preparation of (CdSe)ZnS

A flask containing 5 g of TOPO was heated to 190EC under vacuum for several hours then cooled to 60EC after which 0.5 mL trioctylphosphine (TOP) was added. Roughly 0.1–0.4 :mols of CdSe dots dispersed in hexane were transferred into the reaction vessel via syringe and the solvent was pumped off.

Diethyl zinc ($ZnEt_2$) and hexamethyldisilathiane ($(TMS)_2S$) were used as the Zn and S precursors, respectively. The amounts of Zn and S precursors needed to grow a ZnS shell of desired thickness for each CdSe sample were determined as follows: First, the average radius of the CdSe dots was estimated from TEM or SAXS measurements. Next, the ratio of ZnS to CdSe necessary to form a shell of desired thickness was calculated based on the ratio of the shell volume to that of the core assuming a spherical core and shell and taking into account the bulk lattice parameters of CdSe and ZnS. For larger particles the ratio of Zn to Cd necessary to achieve the same thickness shell is less than for the smaller dots. The actual amount of ZnS that grows onto the CdSe cores was generally less than the amount added due to incomplete reaction of the precursors and to loss of some material on the walls of the flask during the addition.

Equimolar amounts of the precursors were dissolved in 2–4 mL TOP inside an inert atmosphere glove box. The precursor solution was loaded into a syringe and transferred to an addition funnel attached to the reaction flask. The reaction flask containing CdSe dots dispersed in TOPO and TOP was heated under an atmosphere of $N_2$. The temperature at which the precursors were added ranged from 140° C. for 23 Å diameter dots to 220° C. for 55 Å diameter dots. When the desired temperature was reached the Zn and S precursors were added dropwise to the vigorously stirring reaction mixture over a period of 5–10 minutes.

After the addition was complete the mixture was cooled to 90° C. and left stirring for several hours. Butanol (5 mL) was added to the mixture to prevent the TOPO from solidifying upon cooling to room temperature. The overcoated particles were stored in their growth solution to ensure that the surface of the dots remained passivated with TOPO. They were later recovered in powder form by precipitating with methanol and redispersing into a variety of solvents including hexane, chloroform, toluene, THF and pyridine.

EXAMPLE 2

Preparation of a Water-soluble Quantum Dots Using Long Chain Mercaptocarboxylic Acid TOPO capped-(CdSe)ZnS quantum dots were prepared as described in Example 1. The overcoated (CdSe)ZnS dots were precipitated from the growth solution using a mixture of butanol and methanol. To obtain the precipitated quantum dots, the solution was centrifuged for 5–10 min, the supernatant was decanted and the residue was washed with methanol (2×).

The residue was weighed. The weight of the TOPO cap was assumed to be 30% of the total weight; and a 30-fold molar excess of the new capping compound, 11-mercaptoundecanoic acid (MUA) was added. The residue and MUA (neat solution) were stirred at 60° C. for 8–12 hours. A volume of tetrahydrofuran (THF) equal to the added MUA was added to the MUA/dot mixture, with the mixture was still hot. A clear solution resulted and the coated quantum dots were stored under THF.

The coated quantum dots are rendered water-soluble by deprotonation of the carboxylic acid functional group of the MUA. The deprotonation was accomplished by adding a suspension of potassium t-butoxide in THF to the MUA-quantum dot/THF solution. A gel resulted, which was then centrifuged and the supernatant liquid was poured off. The residue was washed twice with THF, centrifuged each time and the supernatant liquid poured off. The final residue was allowed to dry in air for 10 minutes. Deionized water (Millipore) was added to the residue until a clear solution formed.

The resultant coated quantum dots were tested for photoluminescent quantum yield. A CdSe quantum dot with a four monolayer coating of ZnS coated as described had an absorption band a 480 nm and a photoluminescent band at 500 nm, with a quantum yield of 12%. A second CdSe quantum dot with a four monolayer coating of ZnS coated as described had an absorption band a 526 nm and a photoluminescent band at 542 nm, with a quantum yield of 18%.

What is claimed is:

1. A water-soluble semiconductor nanocrystal capable of light emission comprising:
   a quantum dot having a selected band gap energy;
   a layer overcoating the quantum dot, wherein the overcoating layer comprises a material having a band gap energy greater than the band gap energy of the quantum dot; and
   an outer layer, wherein the outer layer comprises a compound having a formula, $SH(CH_2)_nX$, where X is carboxylate or sulfonate and where $n \geq 8$.

2. A water-soluble semiconductor noncrystal capable of light emission comprising:
   a quantum dot having a selected band gap energy;
   a layer overcoating the quantum dot, wherein the overcoating layer comprises a material having a band gap energy greater than the band gap energy of the quantum dot; and
   an outer layer, wherein the outer layer comprises a compound having a formula, $SH(CH_2)_nX$, where X is carboxylate or sulfonate and where $n \geq 10$.

3. The water soluble nanocrystal of claim 1 or 2, wherein the quantum dot comprises YX, where Y is selected from the group consisting of Zn, Cd, and mixtures thereof and X is selected from the group consisting S, Se and Te and mixtures thereof.

4. The water soluble nanocrystal of claim 1 or 2, wherein the overcoating layer comprises AB, where A is selected from the group consisting of Zn, Cd, and mixtures thereof, and B is selected from the group consisting of S, Se and Te, such that AB is not identical to the quantum dot and wherein AB has a higher band gap energy than the quantum dot.

5. The water soluble nanocrystal of claim 4, wherein the overcoating layer comprises up to eight monolayers of AB.

6. The water soluble nanocrystal of claim 1 or 2, wherein a size of the quantum dot is between about 12 Å and about 150 Å.

7. A composition, comprising:
   a water soluble nanocrystal including a quantum dot having a band gap energy in the visible light range and at least one water-solubilizing moiety attached to the outer surface of the quantum dot, the moiety having the formula, $SH(CH_2)_nX$, where X is a hydrophilic moiety and where $n \geq 8$, the water soluble nanocrystal dispersed or dissolved in an aqueous medium.

8. A composition, comprising:
   a water soluble nanocrystal including a quantum dot having a band gap energy in the visible light range and at least one water-solubilizing moiety attached to the outer surface of the quantum dot, the moiety having the formula, $SH(CH_2)_nX$, where X is a hydrophilic moiety and where $n \geq 10$, the water soluble nanocrystal dispersed or dissolved in an aqueous medium.

* * * * *